United States Patent
Kenny et al.

(10) Patent No.: US 7,033,758 B2
(45) Date of Patent: Apr. 25, 2006

(54) HIGHLY SENSITIVE GENE DETECTION AND LOCALIZATION USING IN SITU BRANCHED-DNA HYBRIDIZATION

(75) Inventors: Daryn Kenny, Moraga, CA (US); Lu Ping Shen, San Leandro, CA (US); Vincent P. Antao, Berkeley, CA (US); Audrey N. Player, Silver Springs, MD (US); Wei Cao, Shanghai (CN)

(73) Assignee: Bayer Corporation, Tarrytown, NY (US)

(*) Notice: Subject to any disclaimer, the term of this patent is extended or adjusted under 35 U.S.C. 154(b) by 445 days.

(21) Appl. No.: 09/872,493

(22) Filed: Jun. 1, 2001

(65) Prior Publication Data

US 2002/0172950 A1 Nov. 21, 2002

Related U.S. Application Data

(60) Provisional application No. 60/209,139, filed on Jun. 2, 2000.

(51) Int. Cl.
*C12Q 1/68* (2006.01)
*C07H 21/04* (2006.01)

(52) U.S. Cl. .................. 435/6; 435/91.1; 435/91.2; 536/23.1; 536/24.3

(58) Field of Classification Search .............. 435/6, 435/91.1; 536/23.1, 24
See application file for complete search history.

(56) References Cited

U.S. PATENT DOCUMENTS

| 4,868,105 A | 9/1989 | Urdea et al. |
| 5,124,246 A | 6/1992 | Urdea et al. |
| 5,501,954 A | 3/1996 | Mahr et al. |
| 5,681,702 A | 10/1997 | Collins et al. |
| 5,780,610 A | 7/1998 | Collins et al. |
| 5,849,481 A | 12/1998 | Urdea et al. |
| 5,888,733 A | 3/1999 | Hyldig-Nielsen et al. |
| 5,985,549 A | 11/1999 | Singer et al. |
| 6,022,689 A * | 2/2000 | Sarto et al. ............. 435/6 |

FOREIGN PATENT DOCUMENTS

WO    WO 99/11813    3/1999

OTHER PUBLICATIONS

Nolte, Frederick, "Branched DNA signl amplification for direct quantitation of nuleic acid sequences in clinical specimens." Advances in Clinical Chemistry. vol. 33, pp. 201-235, 1998.*

(Continued)

*Primary Examiner*—Jeanine A. Goldberg
(74) *Attorney, Agent, or Firm*—Reed IP Law Group; Karen Canaan (57) ABSTRACT

Methods are provided for highly sensitive and rapid in situ detection of a nucleic acid analyte of a known sequence. The method employs oligonucleotide probes in a series of optimized steps to amplify a signal and decrease background. Sensitivity is enhanced such that the method can detect as few as 1–2 copies of nucleic acid analyte per sample, the sample containing a cell, tissue or similar biological material. Methods of detecting and identifying the position of the nucleic acid analyte in a cell are also provided.

33 Claims, 7 Drawing Sheets

OTHER PUBLICATIONS

Kern et al. "An enhanced sensitivity branched DNA assay for quantification of HIV." J. of Clin. Microbiol. vol. 34, No. 12, pp. 3196-3202, Dec. 1996.*

Scharen et al. "A single rotocol to detect transcripts of various types and expression levels in neural tissue and cultured cells." Histochemistry. vol. 100, pp. 431-440, 1993.*

Xu et al. "In situ hybridiation of mRNA with hapten labelled probes." In situ hybridization. 2$^{nd}$ Edition, pp. 87-106, 1999.*

Decimo et al. Gene Probes 2. Chapter 8, pp. 183-198, 1996.*

Plummer et al. (Diagnostic Mol. Pathology, vol. 7, No. 2, pp. 76-84, 1998).*

Adler et al. (1997), High Sensitivity Detection of HPV-16 in SiHa and CaSki Cells Utilizing FISH Enhanced by TSA, *Histochem. Cell. Biol. 108*(4-5):321-324.

Collins et al. (1997), "A Branched DNA Signal Amplification Assay for Quantitation of Nucleic Acid Targets Below 100 Molecules/ml," *Nucleic Acids Research 25*(15):2979-2984.

Deichmann et al. (1997), "Ultra-sensitive FISH is a Useful Tool for Studying Chronic HIV-1 Infection," *J. Virol. Methods 65*(1):19-25.

Siadat-Pajouh et al. (1994), "Introduction of a Fast and Sensitive Fluorescent in situ Hybridization Method for Single-copy Detection of Human Papillomavirus (HPV) Genome," *J. Histochem. Cytochem. 42*(11):1503-1512.

Antao et al. (1999), "In Situ Hybridization Using the bDNA Technology," *Techniques in Quantification and Localization of Gene Expression*, pp. 81-93.

Cao et al. (1998), "A Sensitive, Rapid, and Non-Isotopic In Situ bDNA Assay for Detection of hnRNPA2 mRNA," *Proceedings of the American Association for Cancer Research Annual 39*:335, Abstract #2287.

Freeman et al. (1999), The Maturation of Nucleic Acid Technologies, *Trends in Biotechnology 17*(2):44-45, Elsevier, Amsterdam, NL.

Nolte (1998), "Branched DNA Signal Amplification for Direct Quantification of Nucleic Acid Sequences in Clinical Specimens," *Advances in Clinical Chemistry 33*:201-235.

Player et al. (2001), "Single-Copy Gene Detection Using Branched DNA (bDNA) In Situ Hybridization," *The Journal of Histochemistry & Cytochemistry 49*(S):603-611.

Shen et al. (1998), "Quantification of Cytokine mRNA in Peripheral Blood Mononuclear Cells Using Branched DNA (bDNA) Technology," *J. Immunol. Methods 215*(1-2):123-134.

* cited by examiner

HIGHLY SENSITIVE GENE DETECTION AND LOCALIZATION USING IN SITU BRANCHED-DNA HYBRIDIZATION

CROSS REFERENCE TO RELATED APPLICATION

This application claims priority to U.S. Provisional Application Ser. No. 60/209,139, filed Jun. 2, 2000.

TECHNICAL FIELD

This invention relates generally to nucleic acid chemistry and biochemical assays. More particularly, the invention relates to highly sensitive methods for in situ detection of a nucleic acid analyte. The method employs branched-DNA oligoprobes and hybridization techniques to detect and identify the location of a nucleic acid analyte within a biological sample.

BACKGROUND

Branched-DNA (bDNA) signal-amplification technology has been used extensively in a microwell format to detect and quantify specific nucleic acid sequences. Urdea et al. (2000) Branched-DNA (bDNA) Technology. In Kessler C., ed., Nonradioactive Analysis of Biomolecules, New York, Springer-Verlag:388–395. Inherently quantitative and highly reproducible, bDNA can be applied to the detection of any nucleic acid target for which a sequence is known without the use of radioactive probes.

A number of bDNA assays have been developed for the quantification of viral nucleic acids. These include: human immunodeficiency virus type 1 (HIV-1) RNA, Kern et al. (1996) J Clin Microbiol 34:3196–3203; simian immunodeficiency virus (SIV) RNA, Sodora et al. (1998) AIDS Res Hum Retroviruses 14:171–181; hepatitis B virus (HBV) DNA, Hendricks et al. (1995) Am J Clin Pathol 104:537–546; hepatitis C virus (HCV) RNA, Detmer et al. (1996) J Clin Microbio 34:901–907; hepatitis G virus (HGV) RNA, Brandhagen et al. (1999) Am J Gastroenterol 94:1000–1005; and cytomegalovirus (CMV) DNA, Chernoff et al. (1997) J Clin Microbiol 35:2740–2744.

More recently, bDNA technology has been used to detect and measure expression of cellular mRNAs, including: cytokines, Breen et al. (1997) Cell Immunol 178:91–98 and Shen et al. (1998) J Immunol Methods 215:123–134, progesterone and estrogen receptors, Nargessi et al. (1998) Breast Cancer Res Treat 50:47–55 and Nargessi et al. (1998) Breast Cancer Res Treat 50:57–62; insulin, Wang et al. (1997) Proc Natl Acad Sci USA 94:4360–4365; glucokinase, Cabrera-Valladares et al. (1999) Endocrinology 140:3091–3096; c-fos, Shyamala et al. (1999) Anal Biochem 266:140–147; and aP2, Burris et al. (1999) Mol Endocrinol 13:410–417. All of these bDNA assays were developed to measure nucleic acids in serum, plasma or cell lysates. None of these studies, however, suggests or discloses a bDNA assay for the detection of nucleic acids in morphologically intact cells or tissues.

In contrast, an in situ hybridization (ISH) assay would necessarily have the capability to detect specific nucleic acid sequences in morphologically intact cells or tissues. ISH methods have been improved since the general concept was introduced by Pardue and Gall over twenty years ago. Pardue et al. (1969) Proc Natl Acad Sci USA 64:600–604. For example, use of non-isotopic probes has eliminated the inherent problems associated with radioactive ISH methods such as long turn-around times, risk of exposure to radioactivity and waste disposal.

In addition, the incorporation of various target and signal-amplification systems has improved ISH sensitivity. Notwithstanding these advances in ISH methods, however, a number of challenges must still be overcome. These challenges include developing sensitive and specific target detection, ensuring precise co-localization of signal and target, preserving target sequences, and preserving cellular and tissue morphology. In addition, ISH methods must address a number of practical concerns, including ease-of-use, reproducibility and amenability to quantification, amenability to automation, versatility and timely completion.

Catalyzed reporter deposition tyramide signal amplification (CARD/TSA) is one ISH method that has been proposed to address some of these challenges and concerns. Some studies have shown that the CARD/TSA ISH method can detect 1–2 copies of HPV-16 DNA in SiHa cells. Siadat-Pajouh et al. (1994) J Histochem Cytochem 42:1503–1512 and Adler et al. (1997) Histochem Cell Biol 108:321–324.

One study has shown that it is possible to adapt bDNA technology to an ISH format for the detection of mRNA. Cao et al. (1998) Proceedings of the American Association for Cancer Research, 89th meeting, New Orleans, La. and Antao et al. (1999) In Situ Hybridization Using the bDNA Technology. In Patterson, B. K., ed., Techniques in Quantification and Localization of Gene Expression, Boston, Birkhauser Press:81–93. The assay described in this study, however, has relatively low sensitivity.

Thus, there remains a need in the art to provide highly sensitive methods for in situ detection of nucleic acid analytes in biological samples. The present invention satisfies these and other needs in the art.

SUMMARY OF THE INVENTION

Accordingly, it is a primary object of the invention to address the above-described needs in the art by providing a method for in situ detection of a nucleic acid analyte within a sample of biological material based on bDNA hybridization, wherein the method results in increased sensitivity.

It is another object of the invention to provide a method for in situ detection based on bDNA hybridization that has a sensitivity sufficient to detect from 1 to about 10 copies of the nucleic acid analyte per cell.

It is yet another object of the invention to provide a method for in situ detection based on bDNA hybridization that has a sensitivity sufficient to detect from 1 to about 2 copies of the nucleic acid analyte per cell.

It is still another object of the invention to provide a method for identifying the position, i.e., subcellular location, of a nucleic acid analyte within a single cell based on a bDNA hybridization technique.

Additional objects, advantages and novel features of the invention will be set forth in part in the description which follows, and in part will become apparent to those skilled in the art upon examination of the following, or may be learned by practice of the invention.

Accordingly, in a first embodiment, a method is provided for in situ detection of a nucleic acid analyte within a sample of biological material based on bDNA hybridization comprising the steps of:

(a) preparing the sample of biological material by:
  (i) immobilizing the biological material on a substrate;
  (ii) permeabilizing the substrate-bound biological material by contacting the substrate-bound biological material to a solution containing Proteinase K at a concentration of about 0.5 µg/ml to about 50 µg/ml; and
  (iii) optionally heating the permeabilized biological material to a temperature and for a time period effective to denature any double-stranded DNA;
(b) contacting the biological material with a target oligonucleotide probe under hybridizing conditions, wherein at least a portion of the target probe is complementary to at least a portion of the nucleic acid analyte, so that an analyte-target probe complex is formed when the nucleic acid analyte is present in the sample;
(c) washing the biological material with a washing fluid comprising a detergent, at a temperature in the range of approximately 21 to 60° C.; and
(d) detecting any analyte-target probe complex on the substrate.

In addition, the invention provides that step (d), i.e., the detection step, in the above-identified method preferably comprises:
  (d)(i) contacting the washed substrate and analyte-target probe complex with a preamplifier oligonucleotide probe under hybridizing conditions, wherein a first portion of the preamplifier probe is complementary to a portion of the target probe other than the portion of the target probe that is complementary to the nucleic acid analyte, thereby forming an analyte-target probe-preamplifier probe complex when the nucleic acid analyte is present in the sample;
  (d)(ii) contacting the product of step (d)(i) with an amplifier oligonucleotide probe under hybridizing conditions, wherein a first portion of the amplifier probe is complementary to a second portion of the preamplifier probe, thereby forming an analyte-target probe-preamplifier probe-amplifier probe complex when the nucleic acid analyte is present in the sample;
  (d)(iii) contacting the product of step (d)(ii) with a label oligonucleotide probe under hybridizing conditions, wherein a portion of the label probe binds to a second portion of the amplifier probe, thereby forming an analyte-target probe-preamplifier probe-amplifier probe-label probe complex when the nucleic acid analyte is present in the sample;
  (d)(iv) labeling the analyte-target probe-preamplifier probe-amplifier probe-label probe complex with a detectable label; and
  (d)(v) detecting the presence of the label on the substrate.

It is preferred that the nucleic acid analyte is selected from the group consisting of HIV RNA, HIV DNA, HCV RNA, CMV RNA, CMV DNA, HPV RNA, HPV DNA, LAP, IL-2, endogenous genes and segments thereof.

Preferably, the method has a sensitivity sufficient to detect from 1 to about 10 copies of the nucleic acid analyte, with a sensitivity from 1 to about 2 copies most preferred.

In a second embodiment, a method is provided for identifying the position of a nucleic acid analyte within a cell of a sample of biological material based on bDNA hybridization. This method for the localizing or identifying the position of a nucleic acid analyte comprises the same steps as described above with respect to the in situ detection of a nucleic acid analyte.

Once the label is detected, however, the method for localization further comprises: (e) identifying the position of the analyte-target probe complex within a cell of the biological sample as indicative of the position of the nucleic acid analyte in the cell.

In another embodiment, a method is provided for detecting a nucleic acid analyte within a sample of biological material, the method comprising performing bDNA hybridization to detect the nucleic acid analyte in situ, wherein the method has a sensitivity sufficient to detect from about 1 to about 10 copies of the nucleic acid analyte in the biological material.

BRIEF DESCRIPTION OF THE DRAWINGS

FIGS. 5A, 5B, 5C, 4D and 5E are microscopic images of results obtained in Example 4.

DETAILED DESCRIPTION OF THE INVENTION

I. Definitions and Overview

Before describing the present invention in detail, it is to be understood that this invention is not limited to the specific probes, reagents, assay formats, or the like, as such may vary. It is also to be understood that the terminology used herein is for the purpose of describing particular embodiments only and is not intended to be limiting.

It must be noted that, as used in this specification and the appended claims, the singular forms "a", "an" and "the" include plural referents unless the context clearly dictates otherwise. Thus, for example, reference to "an analyte-target probe complex" includes two or more such complexes, reference to a "washing" step includes two or more such washing steps, and the like.

In this specification and the claims that follow, the following terminology will be used in accordance with the definitions set forth below.

"Oligonucleotide" shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of a purine or pyrimidine base, or of a modified purine or pyrimidine base. The oligonucleotides may be single-stranded or double-stranded, typically single-stranded. Also, the oligonucleotides used in the present invention are normally from about 2 to about 100 monomer units, more typically from about 2 to about 80 monomer units, and most typically from about 2 to about 60 monomer units.

The term "nucleic acid analyte" refers to a single- or double-stranded nucleic acid molecule that contains a target nucleotide sequence. The nucleic acid analyte may be from a variety of sources, e.g., biological fluids or solids, foodstuffs, environmental materials, etc. The term "nucleic acid analyte" is used interchangeably herein with the term "analyte."

As used herein, the terms "target region" or "target nucleotide sequence" refer to a probe-binding region contained within the nucleic acid analyte. The target region must be at least 400 bases in length. The term "target sequence" refers to a sequence with which a probe, i.e., a target oligonucleotide probe, will form a stable hybrid under desired conditions.

As used herein, the terms "probe" and "oligonucleotide probe" refer to a structure comprised of an oligonucleotide as defined above that contains a nucleic acid sequence complementary to a portion of a target nucleotide sequence, at least one other probe, or both. The oligonucleotide regions of the probes may be composed of DNA, and/or RNA, and/or synthetic nucleotide analogs.

It will be appreciated that the binding sequences need not have perfect complementarity to provide stable hybrids. In many situations, stable hybrids will form where fewer than about 10% of the bases are mismatches, ignoring loops of four or more nucleotides. Accordingly, the term "complementary" refers to an oligonucleotide that forms a stable duplex with its "complement" under assay conditions, generally where there is about 90% or greater homology.

As used herein, the terms "biological sample" or "biological material" are used interchangeably and each refers to a sample of tissue, cells or fluid isolated from an individual, including but not limited to, for example, plasma, serum, spinal fluid, semen, lymph fluid, the external sections of the skin, secretions of the respiratory tract, secretions of the intestinal tract, secretions of the genitourinary tract, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). It is preferred that the biological sample is in the form of a fluid, e.g., tissue or cells in a fluid, although solid tissue may also be used. Preferred uses of the present method are in detecting and/or quantitating nucleic acids as follows: (a) viral nucleic acids, such as from hepatitis B virus ("HBV"), hepatitis C virus ("HCV"), hepatitis G virus ("HGV"), human immunodeficiency virus ("HIV"), human papilloma virus ("HPV"), and the herpes family of viruses, including herpes zoster (chicken pox), herpes simplex virus types I & II, cytomegalovirus ("CMV"), and Epstein-Barr virus; (b) bacterial nucleic acids, such as chlamydia, *Mycobacterium tuberculosis,* etc.; and (c) numerous human sequences of interest, including lysosomal acid phosphatase ("LAP"), interleukin-2 (IL-2), and interferon-gamma (INF).

The term "hybridizing conditions" is intended to mean those conditions of time, temperature and pH and the necessary amounts and concentrations of reactants and reagents sufficient to allow at least a portion of a probe to anneal with its complementary sequence. As is well known in the art, the time, temperature and pH conditions required to accomplish hybridization depend on the size of the oligonucleotide probe to be hybridized, the degree of complementarity between the oligonucleotide probe and the target, and the presence of other materials in the hybridization reaction admixture. The actual conditions necessary for each hybridization step are well known in the art or can be determined without undue experimentation.

Typical hybridizing conditions include the use of solutions buffered to a pH from about 7 to about 8.5 and are carried out at temperatures from about 30° C. to about 55° C., preferably from about 37° C. to about 55° C. for a time period of from about 1 second to about 1 day, preferably from about 15 minutes to about 16 hours, and most preferably from about 15 minutes to about 3 hours.

"Hybridization conditions" also require an effective buffer. Any buffer that is compatible, i.e., chemically inert, with respect to the probes and other components, yet still allows for hybridization between complementary base pairs, can be used. One particularly preferred buffer, herein referred to as "Hybridization Solution A," comprises 3×SSC, 50% formamide, 10% dextran sulfate (MW 500,000), 0.2% casein, 10 µg/ml poly A, 100 µg/ml denatured salmon sperm DNA wherein 1×SSC is 0.15 M sodium chloride and 0.015 M sodium citrate. Another particularly preferred buffer, herein referred to as "Hybridization Solution B," comprises 5×SSC, 0.1 to 0.3% sodium dodecyl sulfate, 10% dextran sulfate, 1 mM $ZnCl_2$, and 10 mM $MgCl_2$ wherein 1×SSC is as defined above.

"Optional" or "optionally" means that the subsequently described circumstance may or may not occur, so that the description includes instances where the circumstance does occur and instances where it does not. For example, "optionally heating the permeabilized biological material" includes instances where the permeabilized biological material is heated and instances where the permeabilized biological material is not heated.

The method of the present invention is an in situ bDNA hybridization assay. As appreciated in the art, bDNA-based methods effectively provide for amplification of a signal that might otherwise be undetectable with other techniques. Those skilled in the art are familiar with the techniques and materials necessary for conducting bDNA-based assays. Briefly, in bDNA amplification, a target oligonucleotide probe comprises two sites: one for specifically hybridizing with a portion of the nucleic acid analyte, and one for specifically hybridizing with at least one other probe. Additional oligonucleotide probes with unique sites designed to specifically hybridize to different probes may be used, so that as repeated stages of hybridization occur, a branched-DNA structure is formed. The final oligonucleotide probe to be annealed in the branched structure carries at least one detectable label. Thus, the original target molecule gives rise to a multitude of signals, thereby amplifying the signal for facile detection. In addition, reference may be made to the pertinent literature, texts and other references for a description of conventional bDNA techniques. See, for example, Collins et al. (1997) Nucleic Acid Res. 25(15):2979–2984.

The present invention provides highly sensitive techniques for detecting a nucleic acid analyte based on in situ bDNA hybridization. Previous in situ bDNA hybridization techniques have provided relatively insensitive results. The present invention, however, provides an in situ bDNA method that is highly sensitive, e.g., having a sensitivity sufficient to detect from about 1 to about 10 copies of an nucleic acid analyte in a biological material.

II. The Detection Method

In a first embodiment, the invention provides a method for in situ detection of a nucleic acid analyte within a sample of biological material based on bDNA hybridization.

The method comprises the steps of (a) preparing the sample of biological material, (b) contacting the biological material with a target oligonucleotide probe under hybridizing conditions, (c) washing the biological material, and (d) detecting any analyte-target probe complex on the substrate.

The sample of biological material is obtained through conventional processes and includes, for example, biopsy and biological fluid extraction. Because the technique is for in situ analysis, however, tissues, cells or organelles are analyzed rather than a lysate. Care must be taken in obtaining and handling the tissue, cell or organelle throughout the assay to ensure that the material remains substantially intact.

The biological sample for use in the present method, i.e., the tissues or cells to be analyzed, may be taken from any part of the body so long as the biological material is suspected of containing the analyte of interest. For example, suitable tissues for use in the present method include, without limitation, adrenal, bladder, bone marrow, brain, breast, cardiac, colon, esophageal, intestinal, kidney, liver, pulmonary, lymph node, nerve, ovarian, pancreatic, prostatic, skeletal (striated) muscle, smooth muscle, spleen, stomach, testicular, tonsil, tracheal and uterine tissue. Furthermore, cells taken from these same tissues are appropriate for the techniques described herein. Additionally, cells may be obtained from cell-containing fluids such as plasma, serum, spinal fluid, etc., as explained above. Initially, the biological material must be preserved or "fixed." Although many methods are known in the art for fixing biological samples, it is preferred that the biological sample is fixed with formaldehyde. For example, the biological material may be combined with a 4% formaldehyde solution for 30 minutes on ice. Alternatively, other fixatives, e.g., alcohol, may also be employed. Once fixed, the biological material must be immobilized on a substrate. Suitable substrates are comprised of those materials that allow for the immobilization of a tissue, cell or organelle while preserving the sample's morphology. The substrate material must also be solid in addition to being resistant to heat. Furthermore, the substrate must be inert with regard to the reagents used. Preferred substrates comprise glass, e.g., a glass slide, although a resilient plastic may also be used.

The biological material may be immobilized onto the substrate using conventional methods. For cells, it is preferred that the biological material is immobilized using a centrifuge. Generally, the force required to immobilize the biological material onto the substrate is from about 200× g to about 500× g (times the force of gravity). It is preferred that the force used is about 300× g.

Immobilization of tissue samples is preferably carried out by cutting very thin sections of the tissue sample and placing them onto a suitable substrate. Preferably, the tissue is first placed in a cryostat and cooled to about −15° C. to about −20° C. in order to freeze the tissue.

Then, a microtome is used to slice the frozen tissue into sections. Thereafter, a single section is placed onto a substrate, e.g., glass slide, and the section is allowed to "melt" on the substrate, thereby immobilizing the sample. Tissues infused with wax, e.g., paraffin, may be used in place of frozen tissues. As will be appreciated, other methods for immobilizing the tissue sample may be used.

In order to ensure that the oligonucleotide probes have access to the internal milieu, it is necessary to render permeable the substrate-bound biological material. It has been found that contacting the substrate-bound biological material to a solution containing Proteinase K at a concentration of about 0.5 μg/ml to about 50 μg/ml, preferably from about 5 μg/ml to about 20 μg/ml (from a stock solution having an activity of 600 units per ml), renders the biological material permeable to a sufficient degree such that the probes freely pass biological membranes while maintaining sample morphology. The time and temperature parameters for rendering the biological material permeable are well known or can be determined experimentally. A reaction time of about 10 minutes at about 37° C. is preferred for permeabilizing with Proteinase K.

When the nucleic acid analyte comprises double-stranded DNA, it is necessary to denature the DNA such that probe hybridization may take place. Suitable denaturing steps include exposing the sample to an alkali or heat treatment. It has been found, however, that heating the DNA from about 1.5 minutes to about 5 minutes is sufficient to denature double-stranded DNA while preserving cellular components. The temperature may be any temperature known in the art sufficient to denature DNA. It is preferred, however, that the temperature is from about 70° C. to about 92° C., preferably about 80° C. to about 92° C., with a temperature of about 92° C. most preferred.

In addition, when the nucleic acid analyte comprises DNA, it is also necessary to digest any RNA that may be present. By digesting RNA, the probes cannot hybridize to RNA, thereby minimizing potential false positive results. Generally, any method known in the art for digesting RNA may be used. It is preferred, however, that RNase (available from Sigma, Fluka, etc.,) is used. RNase may be added to the sample in an amount of from about 25 μg to about 100 μg (per spot on slide) and allowed to incubate for a period of time and at a temperature sufficient to digest the RNA. It is preferred, however, that about 40 μg (per spot on slide) of RNase is added to the sample and maintained at 37° C. for one hour.

Alternatively, if the nucleic acid analyte comprises RNA, digestion of RNA is not performed. Heating of messenger RNA (mRNA) may be required, however, to remove secondary structure.

Other methods of preparing the biological material may also be used. For example, some preparation steps may be carried out using commercially available kits such as the THINPREP® slide system (Cytyc Corporation, Boxborough, Mass.).

Once prepared, the biological material is placed in contact with a target oligonucleotide probe under hybridizing conditions. The target probe has a portion that is complementary to at least a portion of the target sequence of the nucleic acid analyte. When the nucleic acid analyte of interest is present in the sample, the nucleic acid analyte and target probe hybridize to form an analyte-target probe complex.

The amount of target probes added can be determined experimentally, but it is preferred that approximately 0.1 pmoles to about 10 pmoles are added (per spot on slide) and allowed to incubate for about three hours at 40° C. A preferred reaction medium for this hybridization step is Hybridization Solution A (defined above).

Once a sufficient incubation period has passed, both the substrate and analyte-target probe complex, if present, are washed to facilitate the removal of unbound target probes. The washing step requires the use of a washing fluid that generally comprises a buffer solution and, inter alia, a detergent.

The buffer solution may be any conventional solution known in the art suitable for removing unhybridized oligonucleotide probes. Preferred buffer solutions comprise the salts of alkali metals. Particularly preferred buffer solutions comprise sodium chloride, sodium citrate and combinations thereof.

The detergent is preferably a non-ionic detergent. In addition, it is preferred that the detergent is also a hydrophilic surfactant. Exemplary detergents are polyoxyethylene-based detergents, e.g., BRIJ® and TRITON®. Similar detergents also suitable for use in the present invention are sold under the trade names of TWEEN®, GENAPOL®, IGEPAL CA®, THESIT®, and LUPROL® (all available from commercial suppliers).

Once the washing fluid is determined, the washing step is carried out at least one, preferably two, and most preferably three times. It has been found that the temperature of the wash step influences the sensitivity of the assay. Thus, for the present method, temperatures in the range of from about 21° C. to about 60° C. work well and are preferred. Optimally, the wash step is carried out at room temperature.

Once the washing step is complete, unhybridized target probes are absent. Thus, any method that can detect the analyte-target probe complexes on the substrate may be used to determine the presence of the nucleic acid analyte. It is preferred, however, to add additional oligonucleotide probes such that a branched network is formed. Once a branched network is formed, a plurality of detectable labels is added with the effect of "amplifying" the signal for facile detection. Thus, detecting an analyte-target probe complex can be accomplished by:

(d)(i) contacting the washed substrate and analyte-target probe complex with a preamplifier oligonucleotide probe under hybridizing conditions, wherein a first portion of the preamplifier probe is complementary to a portion of the target probe other than the portion of the target probe that is complementary to the nucleic acid analyte, thereby forming an analyte-target probe-preamplifier probe complex when the nucleic acid analyte is present in the sample;

(d)(ii) contacting the product of step (d)(i) with an amplifier oligonucleotide probe under hybridizing conditions, wherein a first portion of the amplifier probe is complementary to a second portion of the preamplifier probe, thereby forming an analyte-target probe-preamplifier probe-amplifier probe complex when the nucleic acid analyte is present in the sample;

(d)(iii) contacting the product of step (d)(ii) with a label oligonucleotide probe under hybridizing conditions, wherein a portion of the label probe binds to a second portion of the amplifier probe, thereby forming an analyte-target probe-preamplifier probe-amplifier probe-label probe complex when the nucleic acid analyte is present in the sample;

(d)(iv) labeling the analyte-target probe-preamplifier probe-amplifier probe-label probe complex with a detectable label; and (d)(v) detecting the presence of the label on the substrate.

Each of the probe hybridization steps, i.e., steps (d)(i), (d)(ii) and (d)(iii), is carried out under conventional hybridization conditions as discussed above. For these particular hybridization steps, however, it is preferred that each step takes place at about 55° C. with an incubation time of about 25 minutes. It is also preferred that each probe, i.e., preamplifier probe, amplifier probe and label probe, is separately admixed with Hybridization Solution B (defined above) for contacting that probe with the growing complex. Thus, for example, the amplifier probe is admixed with Hybridization Solution B and placed in contact with the analyte-target probe-preamplifier probe complex to form an analyte-target probe-preamplifier probe-amplifier probe complex.

Although the amount of probes admixed can be determined using techniques known in the art, it is preferred that the preamplifier probe and amplifier probe are each added in an amount of approximately 1 fmole to about 10 pmoles (per spot on slide). Most preferably, these probes are each added in an amount of about 1 fmole to about 100 fmoles (per spot on slide).

Labeling is accomplished when the label probe hybridizes to the analyte-target probe-preamplifier probe-amplifier probe complex. The label probe includes one or more detectable labels that directly or indirectly provide for a detectable signal. The labels may be bound, covalently or non-covalently, to the label probe as individual members of the complementary sequence, or may be present as a terminal member or terminal tail having a plurality of labels. Various means for providing labels bound to a probe have been reported in the literature. See, for example, Leary et al. (1983) *Proc Natl Acad Sci USA* 80:4045; Renz et al. (1984) *Nucl Acids Res* 12:3435; Richardson et al. (1983) *Nucl Acids Res* 11:6167; Smith et al. *Nucl Acids Res* (1985) 13:2399; Meinkoth et al. (1984) *Anal Biochem* 138:267.

Labels that may be employed include fluorescers, chemiluminescers, dyes, enzymes, enzyme substrates, enzyme cofactors, enzyme inhibitors, enzyme subunits, metal ions and the like. Illustrative specific labels include fluorescein, rhodamine, Texas red, phycoerythrin, umbelliferone, luminol, NADPH, $\alpha$-$\beta$-galactosidase, horseradish peroxidase, and alkaline phosphatase, among others. An alkaline phosphatase label is particularly preferred.

Detection of the detectable label can be accomplished by any art-known means and is dependent upon the nature of the label. For fluorescers, a large number of fluorometers are available. For chemiluminescers, luminometers or films are available. With enzymes, a fluorescent, chemiluminescent, or colored product can be provided and determined fluorometrically, luminometrically, spectrophotometrically or visually (preferably with the aid of a microscope). For the present method, it is preferred that the alkaline phosphatase substrate is added to detect the presence of the alkaline phosphatase label using bright field or fluorescence microscopy.

In contrast to previous assays, the present method for detecting a nucleic acid analyte is highly sensitive. Previous assays relied on the presence of many—oftentimes hundreds—of copies of the nucleic acid analyte. The present method has been developed to detect relatively few copies. Thus, it is preferred that the method has a sensitivity sufficient to detect from 1 to about 10 copies of the nucleic acid analyte. It is most preferred, however, that the method has a sensitivity sufficient to detect from 1 to about 2 copies of the nucleic acid analyte.

III. Synthesis of the Probes

The sequences of the probes are determined using standard techniques known in the art.

Thus, for example, the target probe sequence will be determined using a known sequence of the analyte of interest specific to that analyte. Those regions of the sequences that are intended to be involved with binding (and thus are complementary to another sequence of oligonucleotides—either a probe or analyte) will each be at least 15 nucleotides, usually at least 20 nucleotides, and not more than about 100 nucleotides. Typically, the binding sequences will be approximately 25 nucleotides in length. They will normally be chosen to bind to different sequences of the analyte and/or to specific and different portions of the various probes. In addition, the oligonucleotides for any given set of probes will optimally have the same melting temperature.

Probes with a second binding sequence are selected to be substantially complementary to the appropriate portion of the probe. The second binding sequence may be contiguous to the first binding sequence, or be spaced therefrom by an intermediate noncomplementary sequence. The probes may include other noncomplementary sequences if desired. These noncomplementary sequences, however, must not hinder the binding of the binding sequences or result in nonspecific binding.

The probes may be prepared by oligonucleotide synthesis or by cloning, with the former preferred. As is now well known in the art, methods for synthesizing oligonucleotides typically involve sequential addition of 3'-blocked and 5'-blocked nucleotide monomers to the terminal 5'-hydroxyl group of a growing oligonucleotide chain, wherein each addition is effected by nucleophilic attack of the terminal 5'-hydroxyl group of the growing chain on the 3'-position of the added monomer, which is typically a phosphorus derivative such as a phosphotriester, phosphoramidite, or the like.

IV. Localization

The present invention also provides a method for determining the location or position of a nucleic acid analyte in a cell. As indicated above, this method comprises the same steps as in situ detection but adds a further step of (e) identifying the position of the analyte-target probe complex within a cell of the biological sample as indicative of the position of the nucleic acid analyte in the cell. Previous in situ detection assays were less precise at demonstrating the subcellular position of the signal. For example, the signal of previous in situ assays may not have been "contained" within the subcellular compartment. Alternatively, the signal of previous in situ assays may have been diffused over a relatively large portion of the cell, thereby making impossible a definitive conclusion concerning the location of the nucleic acid analyte. Because the temperatures for hybridization are low, i.e., generally not exceeding 55° C., and the sample treatment is not harsh, the present method makes possible the ability to determine the location of a single analyte within a cell. Even when the temperature is raised for certain steps, e.g., to about 92° C. when denaturing DNA via heating, the present method still maintains the ability to determine the location of a single analyte within a cell.

V. Utility

The present method can be used to detect any nucleic acid for which the sequence is known. Preferred analytes for which the method is particularly well suited include, but are not limited to, HIV RNA, HIV DNA, HCV RNA, CMV RNA, CMV DNA, HPV RNA, HPV DNA, LAP, IL-2, endogenous genes, gene transcripts and segments thereof.

Given its sensitivity, ease of use, versatility, reliability and rapidity (results are obtained within one day), the present method has wide application in the early detection of cancers and infectious diseases. Single-copy detection is particularly advantageous for viral diseases, e.g., HIV and many others, as diagnosis can be achieved much earlier (when viral loads are relatively low), thereby allowing earlier intervention and treatment. In addition, the present method has applications in the field of therapy selection. For example, the present method can be adapted to quickly and accurately detect the gene copy number of the human epidermal growth factor receptor 2 (HER2/neu). This is useful for deciding whether or not to initiate anti-HER2 therapy, e.g., monoclonal anti-HER2 antibody therapy (Herceptin®, available from Genentech, Inc., South San Francisco, Calif.). Furthermore, by modifying cellular or tissue pretreatment conditions, the present method can detect either mRNA or DNA with the same set of probes.

The present method is highly specific and allows for the precise localization of the target sequence within the cell when a portion of the nucleic acid analyte sequence is known. Further, localization is possible even when there is only a single copy of the nucleic acid analyte in the cell. Thus, such an assay has wide application and is particularly useful in research and medicine. In gene therapies, for example, it is now possible to determine whether the medicinal enters the cytoplasm and/or nucleus.

In addition to detecting for cancers and infectious diseases and assisting with therapy selection, the ability to detect nucleic acids within tissue sections using the present methods has further advantages. For example, in situ detection within a tissue sample demonstrates the extent to which a cancer or infectious pathogen has spread to surrounding areas of the tissue. Such information serves as a prognostic indicator and provides the ability to tailor an appropriate therapeutic approach to the disease.

It is to be understood that, while the invention has been described in conjunction with the preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

All publications mentioned herein, both supra and infra, are hereby incorporated by reference. All ranges identified herein, both supra and infra, are inclusive.

Experimental

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.), but some errors and deviation should be accounted for. Unless indicated otherwise, temperature is expressed in ° C. and pressure is at or near atmospheric pressure at sea level.

Unless otherwise indicated, all starting materials and reagents were obtained commercially (e.g., from Aldrich, Sigma and ICN) and used without further purification. Standard cell culture and cell harvesting procedures were used.

EXAMPLE 1

Detection of HPV DNA by bDNA ISH in Cells

A. Materials and Methods i. Cell Culture

Because they contain different strains and amounts of human papilloma virus (HPV), the human cervical carcinoma cell lines of HeLa, CaSki and SiHa were used to evaluate the present invention. Table 1 describes each cell line.

TABLE 1

| Cell Line* | Viral strain | DNA copies per cell 3 |
|---|---|---|
| CaSki | integrated HPV-16 DNA | 400–600 copies |
| HeLa | integrated HPV-18 DNA | 10–50 copies |
| SiHa | integrated HPV-16 DNA | 1–2 copies |
| C33A (control) | HPV negative | 0 copies |

*All cell lines were obtained from the American Type Cell Culture Collection (ATCC; Manassas, VA) and grown in flasks under conditions generally suggested by the ATCC. When required, cells were detached from the flasks using a mild trypsin treatment.

ii. Oligonucleotide Probes

The HPV-16-specific target probes consisted of a total of 26 DNA oligonucleotide probes covering approximately 90% of the E6 and E7 regions of the HPV genome. These probes were designed by first creating a degenerate consensus sequence based on 23 sequences for the E6 and E7 genes of the HPV-16 genome, retrieved from GenBank using the Genetics Data Environment software (Harvard Genome Laboratory, Cambridge, Mass.). Potential target probe sets were then generated using the ProbeDesigner® Software (Bayer Diagnostics, Emeryville, Calif.), which enables flexible design of bDNA probesets with minimal contribution to background and designates a constant melting temperature of 63±2° C. Final probes were selected after screening the probe sets for possible interactions with the other 39 HPV genotypes using HybSimulator® (Advanced Gene Computing Technologies, Inc., Irvine, Calif.) and human genomic DNA sequences using Blast2™ (National Institutes of Health, Bethesda, Md.).

HPV-18-specific target probes consisted of a total of 32 DNA oligonucleotide probes covering 90% of the E6 and E7 regions of the HPV genome. These probes were designed as described above using a degenerate consensus sequence based on four sequences for the E6 and E7 genes of the HPV-18 genome and a constant melting temperature of 63±2° C.

Other DNA oligonucleotide probes, including the preamplifier, amplifier and alkaline phosphatase (AP)-conjugated label probes, have been described in detail. Collins et al. (1997) *Nucleic Acids Res* 25:2979–2984. To reduce non-specific hybridization, non-natural nucleotides 5-methyl-2'-deoxyisocytidine (isoC) and 2'-deoxyisoguanosine (isoG) were included in the binding sites of the target, preamplifier, amplifier and AP-conjugated label probes.

B. DNA Detection

For DNA detection, harvested cells were fixed with 4% formaldehyde in a phosphate buffer solution (PBS; 0.01 M phosphate buffer, pH 7.5) for 30 minutes on ice, washed twice for 2 minutes each and resuspended in PBS. 200 μl aliquots of the fixed cell suspensions were pipetted into double-spotted cytospin funnels (Shandon; Pittsburgh, Pa.) and centrifuged for 6 minutes at 1500 rpm in a cytospin centrifuge (Shandon) using a calculated force equivalent to 300× g. The cells were dehydrated on slides through a graded series of 70%, 90% and 100% ethanol at room temperature (RT) for 2 minutes each, air-dried at RT for 10 minutes, and stored at −80° C. for up to 2 weeks. Cells were rehydrated on slides through a graded series of 100%, 90% and 70% ethanol at RT for 2 minutes each and washed twice for 2 minutes each in PBS. Slides were incubated at 37° C. for 1 hour in 40 μg/ml RNase (Sigma) in 2×SSC (1×SSC is 0.15 M NaCl, 0.015 M Na-citrate), washed twice for 2 minutes each in PBS, and immersed in a pre-warmed jar containing 7.5 to 10 μg/ml Proteinase K (Boehringer Mannheim, Indianapolis, Ind.) in PBS at 37° C. for 10 minutes. After washing twice for 2 minutes each in PBS, cells were dehydrated on slides through a graded series of 70%, 90% and 100% ethanol at RT for 2 minutes each and air-dried at RT for 10 minutes.

Figure 1:
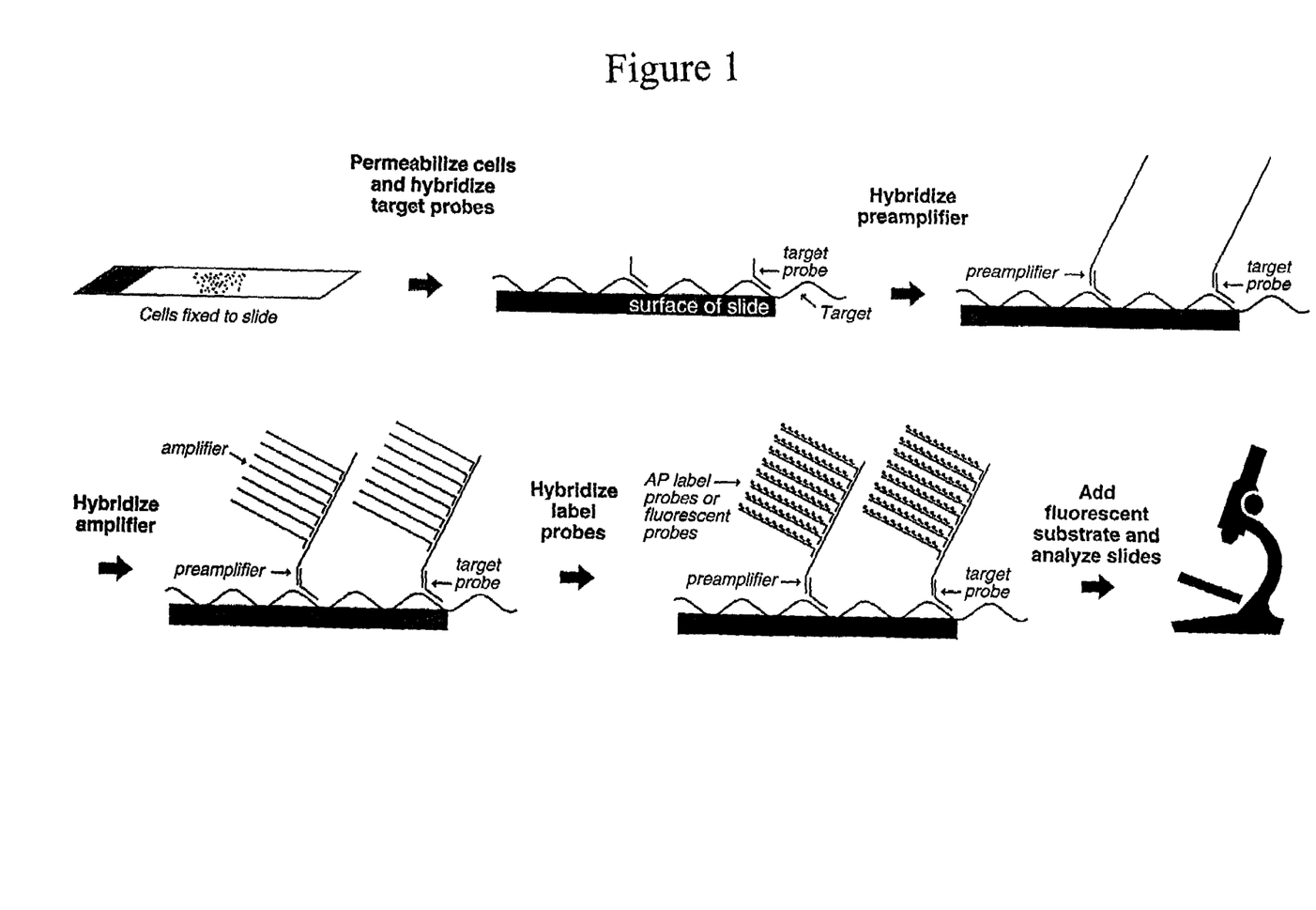
FIG. 1 is a schematic representation of a bDNA ISH method according to the present invention.

After pretreatment, cells were incubated with a prehybridization solution, hybridized with a set of oligonucleotide target probes (described above), followed by hybridization with a series of oligonucleotide probes for signal amplification. As a prehybridization step, each spot on the slide was incubated with 150 μl Hybridization Solution A (3×SSC, 50% formamide, 10% dextran sulfate [MW 500,000], 0.2% casein, 10 μg/ml poly A, 100 μg/ml denatured salmon sperm DNA) at RT for 30 minutes. Slides were transferred to a humidity chamber (Hybaid Omnislide instrument, Phenix Research Products, Hayward, Calif.), incubated at 92° C. for 5 minutes and then removed from the chamber and cooled on the bench top at RT for 5 minutes. The prehybridization solution was removed and each spot on the slide was incubated with 100 μl of Hybridization Solution A containing 0.6 pmole HPV-specific target probes at 40° C. for 3 hours in the humidity chamber. After incubation with target probes, slides were washed at RT with a decreasing series of SSC buffers containing 0.0025% BRIJ®-35 detergent (SURFACT-AMPS®35, 10%, Pierce, Rockford, Ill.) as follows: 3 times for 1–2 minutes with 2×SSC; 3 times for 1–2 minutes with 0.2×SSC; once for 5 minutes with 0.1×SSC; and once for 2 minutes with 2×SSC. Each spot on the slide was incubated with 100 μl Hybridization Solution B (5×SSC, 0.1 to 0.3% sodium dodecyl sulfate [SDS], 10% dextran sulfate, 1 mM $ZnCl_2$, 10 mM $MgCl_2$) containing 90 fmoles preamplifier at 55° C. for 25 minutes in the humidity chamber. Slides were washed twice in 0.1×SSC, 1 mM EDTA for 1 minute and 4 minutes, respectively, and then incubated in 100 μl Hybridization Solution B containing 90 fmoles amplifier at 55° C. for 25 minutes in the humidity chamber. Slides were washed twice in 0.1×SSC, 1 mM EDTA for 1 minute and 4 minutes, respectively, and then incubated in 100 μl Hybridization Solution B containing 90 fmoles AP-conjugated label probe at 55° C. for 15 minutes in the humidity chamber. After washing in Wash D (100 mM tris-(hydroxymethyl)aminomethane, pH 8.0, 0.1% BRIJ®-35, 1 mM $ZnCl_2$, 10 mM $MgCl_2$) at RT for 5 minutes, 50 μl buffered AP substrate (Fast Red, #K597, DAKO Corporation, Carpinteria, Calif.) was added and slides were incubated at RT for 10 minutes according to manufacturer's instructions. Slides were rinsed with water three times for 3 minutes each and then counterstained for 40 seconds with either Gills 1 hematoxylin (American Histology Reagent Company, Inc., Modesto, Calif.) or 0.0001% bisBenzimide (#B2883, Sigma). Slides were mounted with ULTRAMOUNT® (DAKO Corporation), PERMOUNT® (Fisher Scientific) or 75% glycerol and stored at RT. Slides were viewed using a Nikon E800 fluorescence microscope with a FITC or triple-band pass filter (Nikon, Foster City, Calif.) or a 60× bright field objective, and images were captured using an Optronics cooled 3-chip color CCD camera (Optronics Engineering, Goleta, Calif.). Fluorescent or chromogenic images were captured using Image Probe Software (Media Cybernetics, Silver Springs, Mass.). FIG. 1 is a schematic of the assay format for Example 1.

C. Results

Figure 2A:
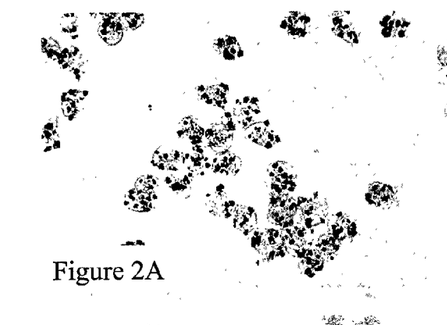
FIGS. 2A, 2B, 2C, 2D, 2E, 2F, 2G and 2H are microscopic (60×) images of results obtained in Example 1.
Figure 2B:
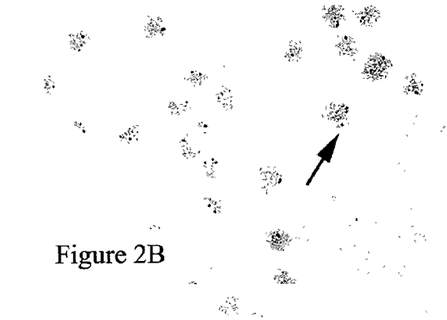
Figure 2C:
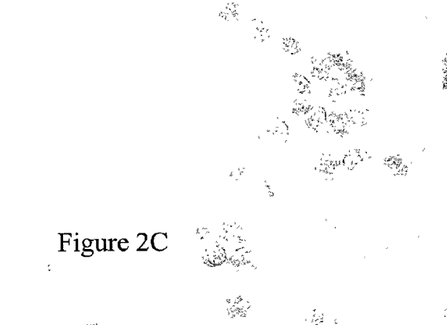
Figure 2D:
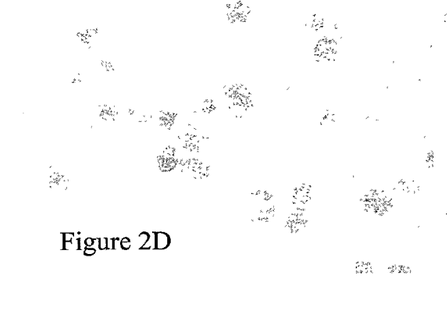

Results of this study demonstrate that upon hybridization with HPV-16 target probes, positive signal detection was observed in CaSki cells (FIG. 2A) and SiHa cells (FIG. 2B). As expected, a multitude of signals were detected in the CaSki cells, as they contain around 400–600 copies of HPV-16. Only one or two signals were detected in the SiHa cells, also as expected, as they contain only 1–2 DNA copies of HPV-16. Finally, no signal was detected with the HPV-16 probes in those cells that lack HPV-16, i.e., HeLa (FIG. 2C) and C33a (FIG. 2D) cells. These results demonstrate both the quantitative capability and specificity of the present method.

Figure 2E:
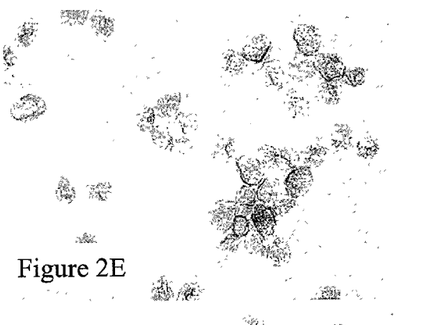
Figure 2F:
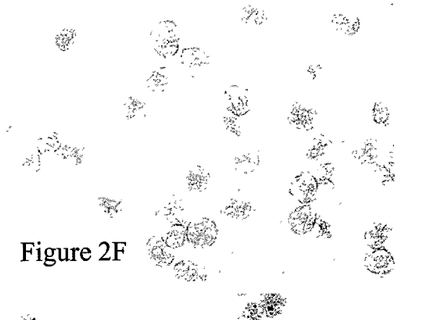
Figure 2G:
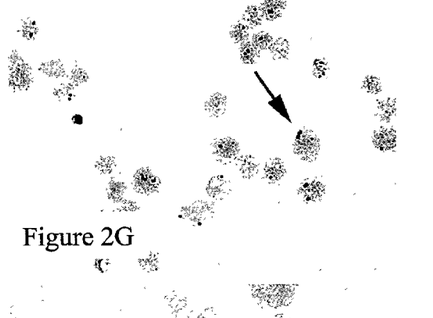
Figure 2H:
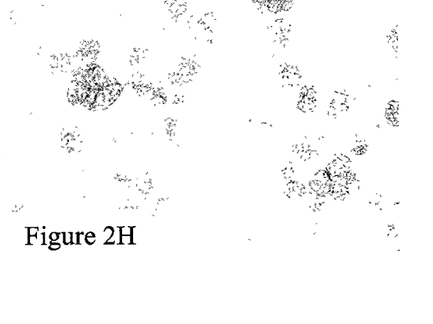

Upon hybridization with HPV-18 target probes, positive signal detection was observed in HeLa cells (FIG. 2G), which contain 10–50 DNA copies of HPV-18. No signal was detected, however, with HPV-18 probes in cells lacking HPV-18, including CaSki (FIG. 2E), SiHa (FIG. 2F) and C33a cells (FIG. 2H). No signal was detected with either HPV-16 or HPV-18 target probes in the HPV-negative HT3 cell line or the ME180 cell line, which harbor a DNA sequence similar to HPV-39 (not shown).

A number of additional controls were performed to demonstrate that the positive signals observed in these experiments were specific for HPV DNA targets. No positive signal was observed when non-specific target probes were used, or when HPV-16 or HPV-18 target probes, amplifier, or AP-conjugated label probes were omitted from the bDNA ISH method. Omission of the Proteinase K digestion or DNA denaturation steps, or treatment of cells with DNase also resulted in a loss of signal. As a further control for the DNase digestion experiments, the RNase treatment step was omitted to confirm that this loss in signal was not due to DNase degradation of the oligonucleotide probes. Under these conditions, positive signal was again detected, indicating that the DNA oligonucleotide probes were not degraded and thus capable of binding to HPV RNA targets.

EXAMPLE 2

Assessing Specificity in Cells

Mixed cell populations were used to further assess the specificity of the present method for HPV DNA detection. Mixed cell samples were comprised of unlabeled CaSki cells (containing 400–600 DNA copies of HPV-16) and labeled HeLa cells (containing 10–50 DNA copies of HPV-18). The HeLa cells were labeled with the fluorescent cell tracer CFDA SE (Carboxyfluorescein diacetate, succinimidyl ester, Molecular Probes, Eugene, Oreg.) according to manufacturer's instructions. Both cell types were assayed according to the procedure of Example 1.

Figure 3A:
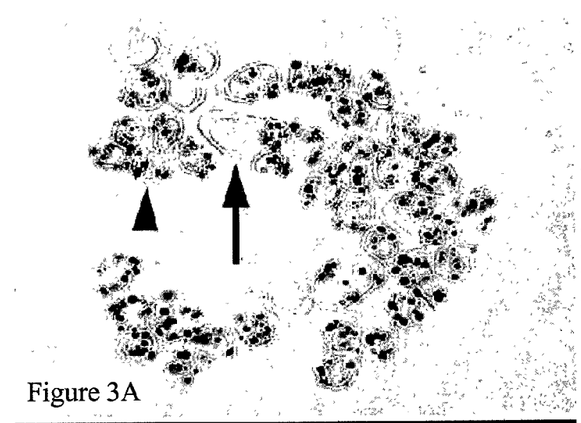
FIGS. 3A, 3B, 3C and 3D are microscopic (60×) images of results obtained in Example 2.
Figure 3B:
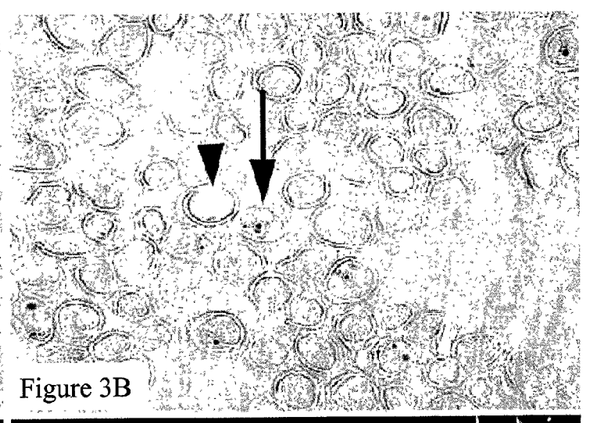
Figure 3C:
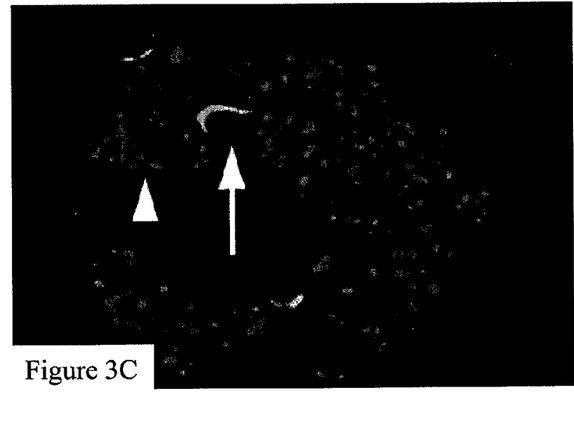
Figure 3D:
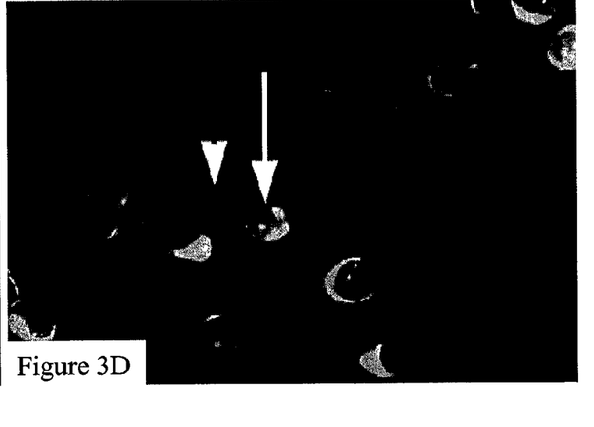

As shown in FIGS. 3A and 3C, hybridization with HPV-16 target probes yielded positive signal detection only in HPV-16-infected CaSki cells (arrow) and not in HeLa cells (arrow). Likewise, as shown in FIGS. 3B and 3D, hybridization with HPV-18 target probes yielded positive signal detection only in HPV-18-infected HeLa cells (arrow head) and not in CaSki cells (arrow head). As expected, greater signal intensity (i.e. larger number and size of spots) was observed for HPV-16 DNA detection in CaSki cells as compared to HPV-18 DNA detection in HeLa cells. This difference in signal intensity is a reflection of the higher number of HPV DNA copies present in CaSki cells (400–600 HPV-16 DNA copies/cell) as compared to HeLa cells (10–50 HPV-18 DNA copies/cell).

These results demonstrate that in a mixed population of cells, the present method can distinguish between cells infected with HPV-16 and cells infected with HPV-18 DNA. Furthermore, there is no transfer of signal from one cell type to another since positive signals are retained only within the appropriate cell types. Moreover, even low abundance targets can be readily detected with the present method without the problems of background or cross-reactivity that could be introduced by the presence of another HPV genotype.

EXAMPLE 3

Detection of HPV RNA and Localization of RNA/DNA within a Cell

For RNA detection, cells grown on chamber slides (#12-565-18, Fisher Scientific, Pittsburgh, Pa.) were fixed with 4% formaldehyde in PBS for 30 minutes at RT, treated with 10 μg/ml Proteinase K in PBS for 10 minutes at RT, and then washed twice for 5 minutes in PBS. Samples were incubated at 40° C. for 3 hours with 1 pmole HPV-specific target probes in a target probe buffer (6×SSC, 25% formamide, 0.2% BRIJ®-35, 0.2% casein), and then washed following the same decreasing series of SSC buffers as described in Example 1. Similarly, the pre-amplifier, amplifier, and AP-conjugated probe hybridization and wash conditions were the same as described in Example 1.

For subcellular localization of DNA targets, HeLa cells were grown overnight on poly-D-lysine-coated chamber slides. Poly-D-lysine is available from Sigma (product code P7280). The following day, the cell culture medium was removed; the cells were washed with PBS, then fixed with 4% formaldehyde in PBS for 30 minutes at RT, and assessed for DNA targets by hybridization with HPV-18 target probes or, as a negative control, HPV-16 target probes.

AP substrate (Fast Red, DAKO Corporation) was added, and slides were incubated at RT for 4 minutes. After stopping the reaction by washing in PBS, samples were postfixed in 4% formaldehyde in PBS for 5 minutes at RT and then counterstained for 40 seconds with either hematoxylin or bisBenzimide. Slides were viewed and images were generated and printed as described in Example 1.

Figure 4A:
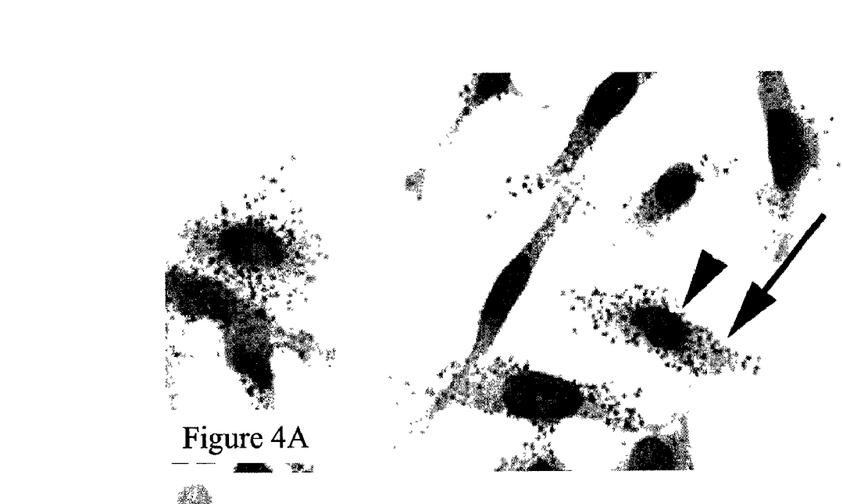
FIGS. 4A, 4B, 4C and 4D are microscopic (60×) images of results obtained in Example 3.
Figure 4B:
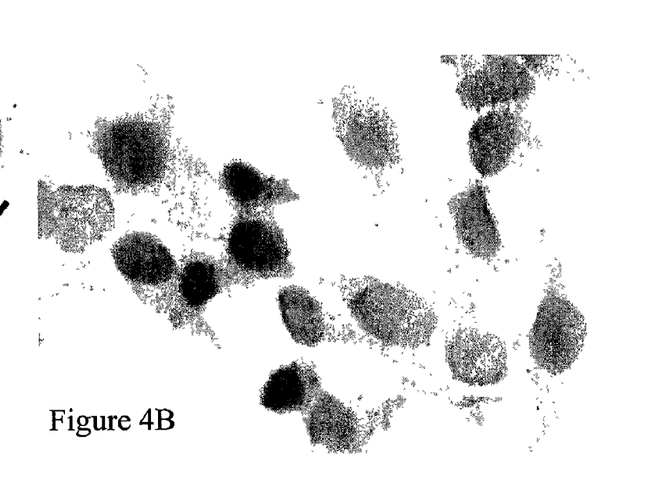

Hybridization of HeLa cells (prepared for RNA detection) with HPV-18 target probes resulted in the detection of HPV-18 mRNA, mainly in the cytoplasm (arrowhead, FIG. 4A). No signal, however, was observed in these same cells incubated with HPV-16 target probes (FIG. 4B).

Figure 4C:
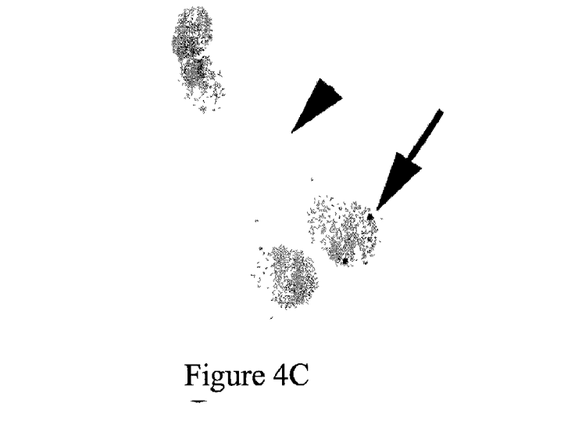
Figure 4D:
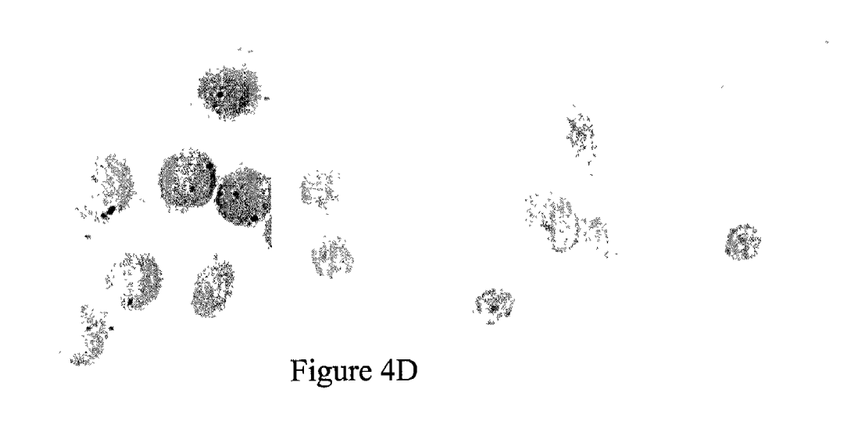

In contrast, hybridization of HeLa cells (prepared for DNA detection) with HPV-18 target probes resulted in the detection of HPV-18 DNA in HeLa cell nuclei (arrow, FIG. 4C). No signal, however, was observed in these same cells incubated with HPV-16 target probes (FIG. 4D).

These results show that HPV mRNA and HPV DNA are localized to different compartments within cells. In particular, viral mRNA is localized predominantly to the cytoplasm, whereas viral DNA is restricted to the nucleus. These results also show that the positive signals are retained within the compartment of the cell in which the target nucleic acid is localized. In other words, the target and signal are co-localized.

The present method provides precise subcellular localization, yielding positive signals retained within the subcellular compartments in which the target nucleic acid sequences are localized.

EXAMPLE 4

Detection of HPV-16 by bDNA ISH in CIN II Specimens

A protocol similar to that of Example 1 was used for in situ hybridization to tissues, as follows. Briefly, formalin-fixed paraffin sections of cervical tissue were de-waxed and rehydrated using standard histology with Xylenes and a graded alcohol series. For DNA detection, the tissue was Rnase-digested at 100 μg/ml Rnase in an Rnase buffer (0.5M NaCl, 10 mM Tris pH 9.0, 1 mM EDTA) at 37° C. for 1 hour, followed by Proteinase K digestion (12 μg/ml in Proteinase K buffer or PBS) at 37° C. for 10 minutes. Proteinase K was inactivated by postfixation in 4% paraformaldehyde in PBS at 4° C. for 10 minutes. Following several washes in PBS, the tissue was acetylated in 1 M TEA as described in Angerer et al. (1987) *In situ Hybridization with RNA Probes-An Annotated Recipe*. In Valentine K. L. et al., eds., *In situ Hybridization-Applications to Neurobiology*, Oxford, Oxford University Press:71–96. Sections were dehydrated in an ethanol series prior to denaturation for 5 minutes at 92°

C. in DB (80% formamide, 2×SSC) on Hybaid (Phenix), followed by immersion in cold 70% ethanol and dehydration. Following a 30-minute incubation in a prehybridization buffer, target oligonucleotide probes were added in fresh prehybridization buffer at a concentration of 10 fmol/μl and coverslipped. Hybridization was carried out in a humidified chamber on a Fisher slide warmer at 37° C. for 1–3 hour(s), with washes and signal amplification the same as previously described in Example 1. Following hybridization, sections were washed in a graded SSC series to 0.1×SSC for a total of 15 minutes of wash time. Hybridization in 1 fmol/μl preamplifier in Hybridization Solution B for 25 minutes at 55° C. was followed by 3 washes in 0.1×SSC for 5 minutes total wash time. Hybridization in 1 fmol/μl amplifier in Hybridization Solution B for 25 minutes at 55° C. was followed by several 0.1×SSC washes. Hybridization in 1 fmol/μl label probe in Hybridization Solution B at 55° C. for 15 minutes was followed by 0.1×SSC Washes and incubation in wash D. Fast Red was prepared immediately prior to application onto sections, and color development was stopped between 4 and 10 minutes. Nuclei were stained in hematoxylin, and slides were coverslipped for microscopy. Endogenous alkaline phosphatase was inactivated with levamisole, 1 μM to 5 μM.

Figure 5A:
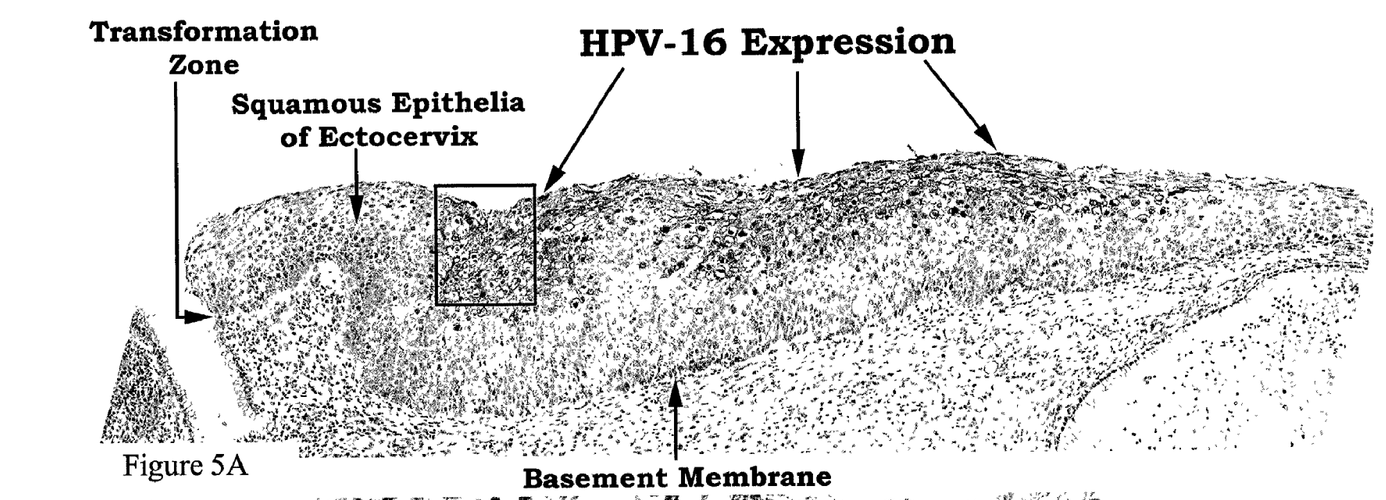
Figure 5B:
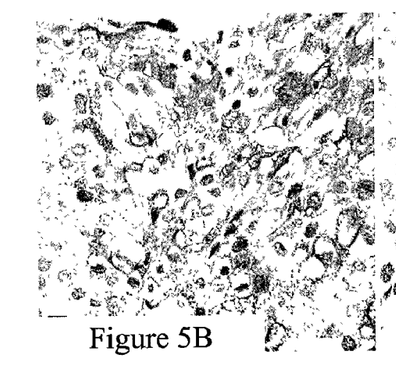
Figure 5C:
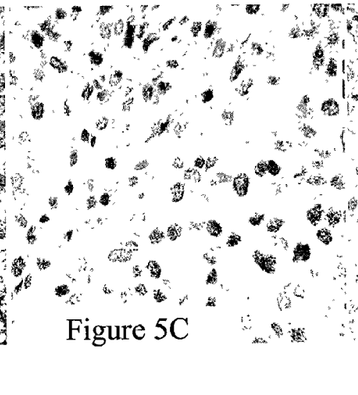
Figure 5D:
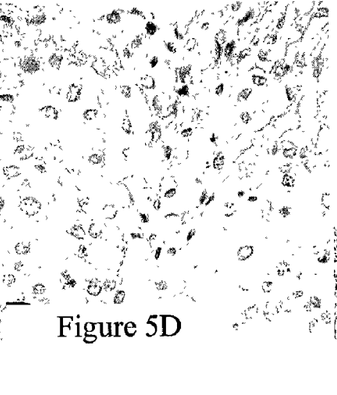
Figure 5E:
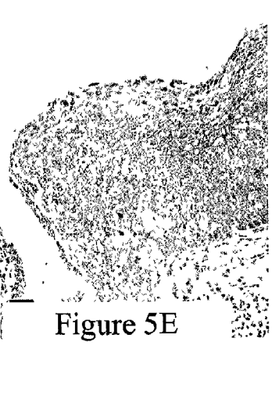

In situ hybridization detected HPV-16 in CIN II (cervical intraepithelial neoplasia) uterine cervix tissue having HPV-associated cytopathic changes (specimen #00B01-627, Clinomics BioSciences, Inc., Pittsfield Mass.). Cell nuclei in each of the sections were stained with hematoxylin. FIG. 5A depicts the distribution of HPV-16 gene expression (stained areas) within squamous epithelia of ectocervix. A higher magnification of the boxed region in FIG. 5A shows the presence of HPV-16 mRNA in the cytosol of some squamous epithelial cells (FIG. 5B). FIG. 5C shows that HPV-16 DNA was detected in the nuclei of squamous cells in a tissue section adjacent to the boxed region in FIG. 5A. HPV-18 DNA, however, was not detected in an adjacent section (FIG. 5D). As expected, GAPDH mRNA was detected throughout the squamous epithelia near the transformation zone (FIG. E). FIGS. 5A and 5E are 200× magnification while FIGS. 5B, 5C and 5D are 600× magnification.

EXAMPLE 5

BDNA ISH of HPV DNA with Preservation of Histopathology

Figure 6A:
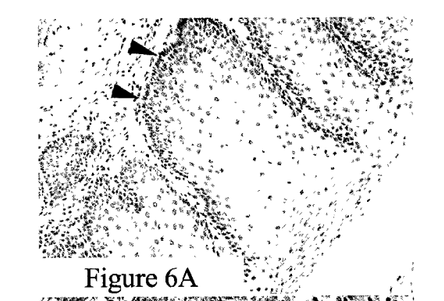
FIGS. 6A, 6B and 6C are microscopic images of results obtained in Example 5.
Figure 6B:
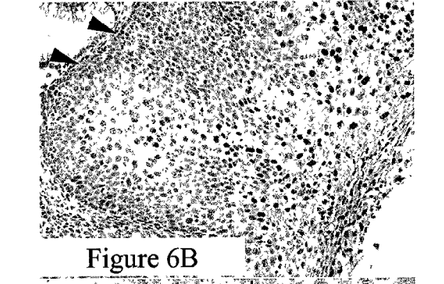
Figure 6C:
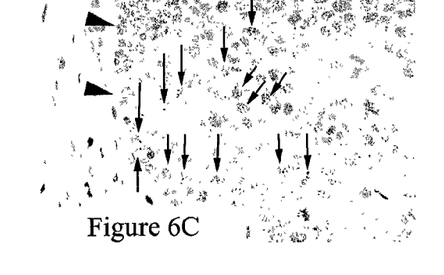

In situ hybridization using the method similar to that of Example 4 was carried out to detect HPV-16 DNA in regions of cytopathic changes characteristic of CIN II lesions in uterine cervix tissue having HPV-associated cytopathic changes (specimen #00B01-624, Clinomics BioSciences, Inc., Pittsfield Mass.), as follows. Cell nuclei in sections were stained with hematoxylin. Large arrowheads indicate contiguous basal cells along the basement membrane that separates the squamous epithelia from underlying stroma. In a region of apparently normal squamous maturation, HPV-16 DNA was not detected, basal cells were restricted near the basement membrane, and the apical portion of epithelia was primarily comprised of differentiated squamous cells with a characteristically large cytosol (FIG. 6A). A nearby region of the same tissue section exhibited abnormal squamous maturation characteristic of moderate dysplasia of the cervix (CIN II) (FIG. 6B). This dysplastic region exhibited overgrowth of basal cells, mixing of basal cells and differentiated squamous cells in the apical epithelial region, and the presence of HPV-16 DNA (stained area) (FIG. 6B). Higher magnification showed the presence of HPV-16 DNA in basal cells, as indicated by smaller arrows (FIG. 6C). FIGS. 6A and 6B are 400× magnification and FIG. 6C is 600× magnification.

EXAMPLE 6

Assessing Specificity in Tissues

Figure 7A:
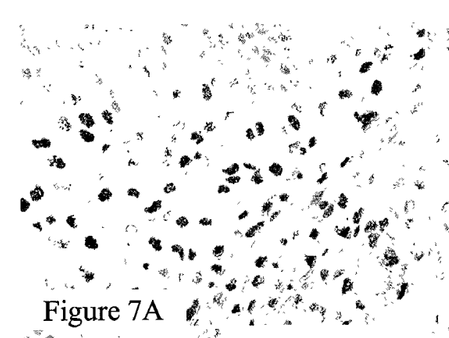
FIGS. 7A, 7B, 7C, 7D, 7E, 7F and 7G are microscopic images of results obtained in Example 6.
Figure 7B:
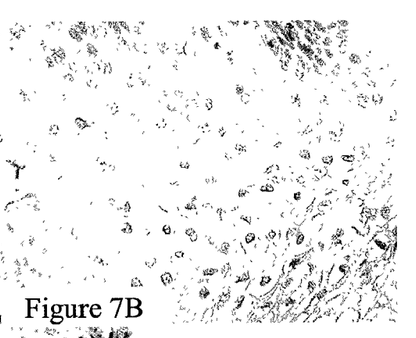
Figure 7C:
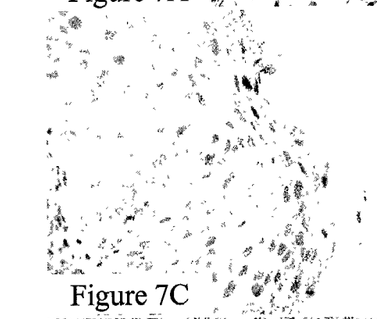
Figure 7D:
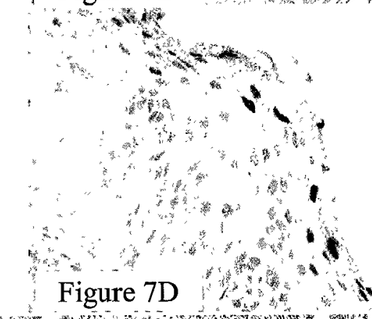
Figure 7E:
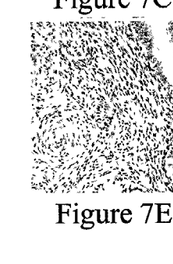
Figure 7F:
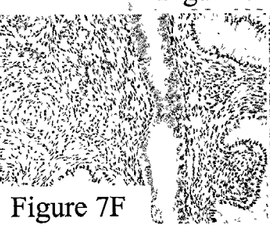
Figure 7G:
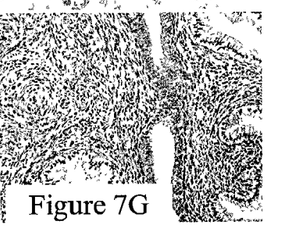

In situ hybridization using genotype-specific HPV probes and the method of Example 4 was used to detect HPV DNA in CIN II tissue sections and in normal cervix sections. Cell nuclei in sections were counterstained with hematoxylin. Stained areas indicated the presence of the target nucleic acid, either viral DNA (FIGS. 7A, 7B, 7C, 7D, 7E and 7F) or endogenous mRNA (FIG. 7G). HPV-16 DNA was detected in squamous ectocervical epithelia of CIN II tissue #00B01-624 (FIG. 7A), but HPV-18 was not detected (FIG. 7B). HPV-18 DNA was detected in CIN II tissue having HPV-associated cytopathic changes (specimen #00B01-625, Clinomics BioSciences, Inc., Pittsfield, Mass.) as shown in FIG. 7D, but HPV-16 was not detected (FIG. 7C). As expected, HPV DNA was not detected in normal cervical tissue (specimen #H-1188-88, Clinomics BioSciences, Inc., Pittsfield Mass.) when tested with HPV-18 (FIG. 7E) or HPV-16 (FIG. 7F) probes. As expected, endogenous GAPDH mRNA was detected in normal cervical tissue (FIG. 7G).

What is claimed is:

1. A method for in situ detection of a nucleic acid analyte within a sample of biological material using bDNA hybridization comprising the steps of:
   (a) preparing the sample of biological material by:
      (i) immobilizing the biological material on a substrate,
      (ii) permeabilizing the substrate-bound biological material by contacting the substrate-bound biological material to a solution containing Proteinase K at a concentration of about 0.5 μg/ml to about 50 μg/ml,
      (iii) digesting any RNA in the sample with RNase; and
      (iv) heating the permeabilized biological material to a temperature and for a time period effective to denature any double-stranded DNA;
   (b) contacting the biological material with a target oligonucleotide probe under hybridizing conditions, wherein at least a portion of the target probe is complementary to at least a portion of the nucleic acid analyte, so that an analyte-target probe complex is formed when the nucleic acid analyte is present in the sample;
   (c) washing the biological material with a washing fluid comprising a detergent, at a temperature in the range of approximately 21 to 60° C.; and
   (d) detecting any analyte-target probe complex on the substrate by:
      (i) contacting the washed substrate and analyte-target probe complex with a preamplifier oligonucleotide probe under hybridizing conditions, wherein a first portion of the preamplifier probe is complementary to a portion of the target probe other than the portion of the target probe that is complementary to the nucleic acid analyte, thereby forming an analyte-target probe-preamplifier probe complex when the nucleic acid analyte is present in the sample,
      (ii) contacting the product of step (d)(i) with an amplifier oligonucleotide probe under hybridizing conditions, wherein a first portion of the amplifier probe is complementary to a second portion of the preamplifier probe, thereby forming an analyte-target probe-preamplifier probe-amplifier probe complex when the nucleic acid analyte is present in the sample,
(iii) contacting the product of step (d)(ii) with a label probe comprised of an alkaline phosphatase conjugated (AP-conjugated) oligonucleotide probe under hybridizing conditions, wherein a portion of the label probe binds to a second portion of the amplifier probe, thereby forming an analyte-target probe-preamplifier probe-amplifier probe-label probe complex when the nucleic acid analyte is present in the sample,
(iv) labeling the analyte-target probe-preamplifier probe-amplifier probe-label probe complex with a detectable label comprised of Fast Red, and
(v) detecting the presence of the label on the substrate, wherein the nucleic acid analyte is selected from the group consisting of DNA, endogenous genes, and segments thereof.

2. The method of claim 1, wherein the nucleic acid analyte is selected from the group consisting of HIV DNA, CMV DNA, HPV DNA, LAP, and IL-2.

3. The method of claim 1, wherein the substrate comprises glass or a resilient plastic.

4. The method of claim 1, wherein the concentration of Proteinase K is from about 5 µg/ml to about 20 µg/ml.

5. The method of claim 1, wherein approximately 0.1 pmoles to 10 pmoles of the target probe is used.

6. The method of claim 1, wherein the detergent in the washing fluid is a hydrophilic surfactant.

7. The method of claim 6, wherein the hydrophilic surfactant is non-ionic.

8. The method of claim 1, wherein the washing fluid is a buffer solution.

9. The method of claim 9, wherein the buffer solution comprises the salts of alkali metals.

10. The method of claim 1, wherein step (c) is repeated at least once.

11. The method of claim 10, wherein step (c) is repeated at least twice.

12. The method of claim 1, wherein approximately 1 fmole to about 10 pmoles of the preamplifier oligonucleotide probe is used.

13. The method of claim 1, wherein approximately 1 fmole to about 10 pmoles of the amplifier oligonucleotide probe is used.

14. The method of claim 1, having a sensitivity sufficient to detect from 1 to about 10 copies of the nucleic acid analyte.

15. The method of claim 14, having a sensitivity sufficient to detect from 1 to about 2 copies of the nucleic acid analyte.

16. The method of claim 1, wherein the biological sample comprises a cell.

17. The method of claim 16, wherein the cell is isolated from the group consisting of plasma, serum, spinal fluid, semen, lymph fluid, the external sections of the skin, secretions of the respiratory tract, secretions of the intestinal tract, secretions of the genitourinary tract, tears, saliva, milk, blood cells, tumors, organs and in vitro cell culture constituents.

18. The method of claim 16, wherein the cell is selected from the group consisting of adrenal, bladder, bone marrow, brain, breast, cardiac, colon, esophageal, intestinal, kidney, liver, pulmonary, lymph node, nerve, ovarian, pancreatic, prostatic, skeletal muscle, smooth muscle, spleen, stomach, testicular, tonsil, tracheal and uterine cells.

19. The method of claim 16, wherein step (a)(i) is carried out using a centrifuge.

20. The method of claim 1, wherein the biological sample comprises a tissue.

21. The method of claim 20, wherein the tissue is selected from the group consisting of adrenal, bladder, bone marrow, brain, breast, cardiac, colon, esophageal, intestinal, kidney, liver, pulmonary, lymph node, nerve, ovarian, pancreatic, prostatic, skeletal muscle, smooth muscle, spleen, stomach, testicular, tonsil, tracheal and uterine tissues.

22. The method of claim 20, wherein step (a)(i) is carried out using sections of the tissue.

23. A method for identifying the position of a nucleic acid analyte within a cell using bDNA hybridization comprising the steps of:
(a) preparing a sample of biological material by:
(i) immobilizing the biological material on a substrate,
(ii) permeabilizing the substrate-bound biological material by contacting the substrate-bound biological material to a solution containing Proteinase K at a concentration of about 0.5 µg/ml to about 50 µg/ml, and
(iii) optionally heating the permeabilized biological material to a temperature and for a time period effective to denature any double-stranded DNA or to remove mRNA secondary structure;
(b) contacting the biological material with a target oligonucleotide probe under hybridizing conditions, wherein at least a portion of the target probe is complementary to at least a portion of the nucleic acid analyte, so that an analyte-target probe complex is formed when the nucleic acid analyte is present in the sample;
(c) washing the biological material with a washing fluid comprising a detergent, at a temperature in the range of approximately 21 to 60° C.;
(d) detecting any analyte-target probe complex on the substrate by:
(i) contacting the washed substrate and analyte-target probe complex with a preamplifier oligonucleotide probe under hybridizing conditions, wherein a first portion of the preamplifier probe is complementary to a portion of the target probe other than the portion of the target probe that is complementary to the nucleic acid analyte, thereby forming an analyte-target probe-preamplifier probe complex when the nucleic acid analyte is present in the sample,
(ii) contacting the product of step (d)(i) with an amplifier oligonucleotide probe under hybridizing conditions, wherein a first portion of the amplifier probe is complementary to a second portion of the preamplifier probe, thereby forming an analyte-target probe-preamplifier probe-amplifier probe complex when the nucleic acid analyte is present in the sample,
(iii) contacting the product of step (d)(ii) with a label probe comprised of an alkaline phosphatase conjugated (AP-conjugated) oligonucleotide probe under hybridizing conditions, wherein a portion of the label probe binds to a second portion of the amplifier probe, thereby forming an analyte-target probe-preamplifier probe-amplifier probe-label probe complex when the nucleic acid analyte is present in the sample,
(iv) labeling the analyte-target probe-preamplifier probe-amplifier probe-label probe complex with a detectable label comprised of Fast Red, and
(v) detecting the presence of the label on the substrate; and
(e) identifying the position of the analyte-target probe complex within the cell, wherein the position of the analyte-target probe complex as determined by the presence of the label is indicative of the position of the nucleic acid analyte within the cell.

24. A method for detecting a nucleic acid analyte within a sample of biological material comprising performing bDNA hybridization to detect the nucleic acid analyte in situ, wherein the method has a sensitivity sufficient to detect from about 1 to about 10 copies of the nucleic acid analyte in the biological material, the bDNA hybridization comprised of the steps of:
(a) preparing the sample of biological material by:
  (i) immobilizing the biological material on a substrate,
  (ii) permeabilizing the substrate-bound biological material by contacting the substrate-bound biological material to a solution containing Proteinase K at a concentration of about 0.5 µg/ml to about 50 µg/ml, and
  (iii) optionally heating the permeabilized biological material to a temperature and for a time period effective to denature any double-stranded DNA or to remove mRNA secondary structure;
(b) contacting the biological material with a target oligonucleotide probe under hybridizing conditions, wherein at least a portion of the target probe is complementary to at least a portion of the nucleic acid analyte, so that an analyte-target probe complex is formed when the nucleic acid analyte is present in the sample;
(c) washing the biological material with a washing fluid comprising a detergent, at a temperature in the range of approximately 21 to 60° C.;
(d) detecting any analyte-target probe complex on the substrate by:
  (i) contacting the washed substrate and analyte-target probe complex with a preamplifier oligonucleotide probe under hybridizing conditions, wherein a first portion of the preamplifier probe is complementary to a portion of the target probe other than the portion of the target probe that is complementary to the nucleic acid analyte, thereby forming an analyte-target probe-preamplifier probe complex when the nucleic acid analyte is present in the sample,
  (ii) contacting the product of step (d)(i) with an amplifier oligonucleotide probe under hybridizing conditions, wherein a first portion of the amplifier probe is complementary to a second portion of the preamplifier probe, thereby forming an analyte-target probe-preamplifier probe-amplifier probe complex when the nucleic acid analyte is present in the sample,
  (iii) contacting the product of step (d)(ii) with a label probe comprised of an alkaline phosphatase conjugated (AP-conjugated) oligonucleotide probe under hybridizing conditions, wherein a portion of the label probe binds to a second portion of the amplifier probe, thereby forming an analyte-target probe-preamplifier probe-amplifier probe-label probe complex when the nucleic acid analyte is present in the sample,
  (iv) labeling the analyte-target probe-preamplifier probe-amplifier probe-label probe complex with a detectable label comprised of Fast Red, and
  (v) detecting the presence of the label on the substrate.

25. The method of claim 24, wherein the nucleic acid analyte is selected from the group consisting of HIV RNA, HIV DNA, HCV RNA, CMV RNA, CMV DNA, HPV RNA, HPV DNA, LAP, IL-2, endogenous genes and segments thereof.

26. The method of claim 24, wherein the sensitivity is sufficient to detect from 1 to about 2 copies of the nucleic acid analyte.

27. The method of claim 24, wherein the biological material comprises a cell.

28. The method of claim 27, wherein the cell is isolated from the group consisting of plasma, serum, spinal fluid, semen, lymph fluid, the external sections of the skin, secretions of the respiratory tract, secretions of the intestinal tract, secretions of the genitourinary tract, tears, saliva, milk, blood cells, tumors, organs and in vitro cell culture constituents.

29. The method of claim 27, wherein the cell is selected from the group consisting of adrenal, bladder, bone marrow, brain, breast, cardiac, colon, esophageal, intestinal, kidney, liver, pulmonary, lymph node, nerve, ovarian, pancreatic, prostatic, skeletal muscle, smooth muscle, spleen, stomach, testicular, tonsil, tracheal and uterine cells.

30. The method of claim 24, wherein the biological sample comprises a tissue.

31. The method of claim 30, wherein the tissue is selected from the group consisting of adrenal, bladder, bone marrow, brain, breast, cardiac, colon, esophageal, intestinal, kidney, liver, pulmonary, lymph node, nerve, ovarian, pancreatic, prostatic, skeletal muscle, smooth muscle, spleen, stomach, testicular, tonsil, tracheal and uterine tissues.

32. The method of claim 23, wherein the nucleic acid analyte is located within a subcellular compartment of the cell.

33. The method of claim 24, wherein the signal and the nucleic acid analyte are co-localized within the subcellular compartment.

* * * * *